United States Patent [19]

Cole

[11] Patent Number: 5,866,765

[45] Date of Patent: Feb. 2, 1999

[54] HYBRID SUNFLOWER PLANT AND SEED (63A51)

[75] Inventor: Glenn S. Cole, Woodland, Calif.

[73] Assignee: Pioneer Hi-Bred International, Inc., Des Moines, Iowa

[21] Appl. No.: 783,915

[22] Filed: Jan. 17, 1997

[51] Int. Cl.$^6$ .............................. A01H 1/02; A01H 5/10; A01H 1/00; C12N 5/04

[52] U.S. Cl. ................. 800/200; 800/255; 800/DIG. 14; 47/58; 47/DIG. 1; 435/412; 435/424; 435/430; 435/430.1

[58] Field of Search .................................. 800/200, 255, 800/205, DIG. 14, DIG. 69; 47/58, DIG. 1; 435/412, 424, 430, 431

[56] References Cited

U.S. PATENT DOCUMENTS 5,461,171  10/1995  Heaton et al. ........................... 554/224

OTHER PUBLICATIONS

Phillips et al. 'Cell/Tissue Culture and In vitro Manipulation. ASA Pub #18, p. 358, 1988.

Report No. 16, Manitoba Regional Sunflower Performance Tests—1995, Sponsored by the Manitoba Sunflower Committee (Jan. 2, 1996).

*Primary Examiner*—Gary Benzion
*Attorney, Agent, or Firm*—Pioneer Hi-Bred International, Inc.

[57] ABSTRACT

According to the invention, there is provided a hybrid sunflower plant, designated as 63A51, produced by crossing two Pioneer Hi-Bred International, Inc. proprietary inbred sunflower lines. This invention relates to the hybrid seed 63A51, the hybrid plant produced from the seed, and variants, mutants, and trivial modifications of hybrid 63A51.

7 Claims, No Drawings

HYBRID SUNFLOWER PLANT AND SEED (63A51)

FIELD OF THE INVENTION

This invention is in the field of sunflower breeding, specifically relating to a hybrid sunflower line designated 63A51.

BACKGROUND OF THE INVENTION

Plant Breeding

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Sunflower (*Heliathus annuus* L.), can be bred by both self-pollination and cross-pollination techniques. The sunflower head (inflorescence) usually is composed of about 1,000 to 2,000 individual disk flowers joined to a common base (receptacle). The flowers around the circumference are ligulate ray flowers with neither stamens nor pistil. The remaining flowers are hermaphroditic and protandrous disk flowers.

Natural pollination of sunflower occurs when flowering starts with the appearance of a tube partly exerted from the sympetalous corolla. The tube is formed by the five syngenesious anthers, and pollen is released on the inner surface of the tube. The style lengthens rapidly and forces the stigma through the tube. The two lobes of the stigma open outward and are receptive to pollen but out of reach of their own pollen initially. Although this largely prevents self-pollination of individual flowers, flowers are exposed to pollen from other flowers on the same head by insects, wind, and gravity.

The development of a hybrid sunflower variety involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with unrelated inbred lines to produce the hybrid progeny ($F_1$). During the inbreeding process in sunflower, the vigor of the lines decreases. Vigor is restored when two different inbred lines are crossed to produce the hybrid progeny ($F_1$). An important consequence of the homozygosity and homogeneity of the inbred lines is that the hybrid created by crossing a defined pair of inbreds will always be the same. Once the inbreds that create a superior hybrid have been identified, a continual supply of the hybrid seed can be produced using these inbred parents and the hybrid corn plants can then be generated from this hybrid seed supply.

Large scale commercial sunflower hybrid production, as it is practiced today, requires the use of some form of male sterility system which controls or inactivates male fertility. A reliable method of controlling male fertility in plants also offers the opportunity for improved plant breeding. This is especially true for development of sunflower hybrids, which relies upon some sort of male sterility system. Two types of male sterility, genetic and cytoplasmic, have been found in sunflower.

Hybrid sunflower seed is typically produced by a male sterility system incorporating genetic or cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in sunflower plants, since only the female provides cytoplasm to the fertilized seed. CMS plants are fertilized with pollen from another inbred that is not male-sterile. Pollen from the second inbred may or may not contribute genes that make the hybrid plants male-fertile.

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. These and all patents referred to are incorporated by reference. In addition to these methods, Albertsen et al., of Pioneer Hi-Bred, U.S. patent application No. 07/848,433, have developed a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

There are many other methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 publication no. 329, 308 and PCT application PCT/CA90/000037 published as WO 90/08828)

The use of male sterile inbreds is but one factor in the production of sunflower hybrids. The development of sunflower hybrids requires, in general, the development of homozygous inbred lines, the crossing of these lines, and the evaluation of the crosses. Breeding programs combine the genetic backgrounds from two or more inbred lines or various other broad-based sources into breeding pools from which new inbred lines are developed by selfing and selection of desired phenotypes. The new inbreds are crossed with other inbred lines and the hybrids from these crosses are evaluated to determine which of those have commercial potential.

There are many important factors to be considered in the art of plant breeding, such as the ability to recognize important morphological and physiological characteristics, the ability to design evaluation techniques for genotypic and phenotypic traits of interest, and the ability to search out and exploit the genes for the desired traits in new or improved combinations.

The objective of commercial sunflower hybrid line development programs is to develop new inbred lines to produce hybrids that combine to produce high yields and superior agronomic performance. The primary trait breeders seek is yield. However, many other major agronomic traits are of importance in hybrid combination and have an impact on yield or otherwise provide superior performance in hybrid combinations. Major objectives in sunflower breeding include improved seed yield, earlier maturity, shorter plant height, uniformity of plant type, and disease and insect resistance. In addition, the lines per se must have acceptable performance for parental traits such as seed yields and pollen production, all of which affect ability to provide parental lines in sufficient quantity and quality for hybridization. These traits have been shown to be under genetic control and many if not all of the traits are affected by multiple genes.

Pedigree Breeding

The pedigree method of breeding is the mostly widely used methodology for new hybrid line development.

In general terms this procedure consists of crossing two inbred lines to produce the non-segregating $F_1$ generation, and self pollination of the $F_1$ generation to produce the $F_2$ generation that segregates for all factors for which the inbred parents differ. An example of this process is set forth below. Variations of this generalized pedigree method are used, but all these variations produce a segregating generation which contains a range of variation for the traits of interest.

EXAMPLE 1

Hypothetical example of pedigree breeding program

Consider a cross between two inbred lines that differ for alleles at six loci. The parental genotypes are:

Parent1 AbCdeF/AbCdeF
Parent2 aBcDEf/aBcDEf
the $F_1$ from a cross between these two parents is:
$F_1$ AbCdeF/aBcDEf
Selfing $F_1$ will produce an $F_2$ generation including the following genotypes:
ABcDEf/abCdeF
ABcDef/abCdEF
ABcDef/abCdeF
The number of genotypes in the $F_2$ is $3^6$ for six segregating loci (729) and will produce $(2^6)-2$ possible new inbreds, (62 for six segregating loci).

Each inbred parent which is used in breeding crosses represents a unique combination of genes, and the combined effects of the genes define the performance of the inbred and its performance in hybrid combination. There is published evidence (Smith, O. S., J. S. C. Smith, S. L. Bowen, R. A. Tenborg and S. J. Wall, TAG 80:833–840 (1990)) that each of the lines are different and can be uniquely identified on the basis of genetically-controlled molecular markers.

It has been shown that most traits of economic value in sunflower are under the genetic control of multiple genetic loci, and that there are a large number of unique combinations of these genes present in elite sunflower germplasm. If not, genetic progress using elite inbred lines would no longer be possible. Studies by Duvick and Russell (Duvick, D. N., *Maydica* 37:69–79, (1992); Russell, W. A., *Maydica* XXIX:375–390 (1983)) have shown that over the last 50 years the rate of genetic progress in commercial hybrids has been between one and two percent per year.

The number of genes affecting the trait of primary economic importance in sunflower yield, has been estimated to be in the range of 10–1000(?). Inbred lines which are used as parents for breeding crosses differ in the number and combination of these genes. These factors make the plant breeder's task more difficult. Compounding this is evidence that no one line contains the favorable allele at all loci, and that different alleles have different economic values depending on the genetic background and field environment in which the hybrid is grown. Fifty years of breeding experience suggests that there are many genes affecting yield and each of these has a relatively small effect on this trait. The effects are small compared to breeders' ability to measure yield differences in evaluation trials. Therefore, the parents of the breeding cross must differ at several of these loci so that the genetic differences in the progeny will be large enough that breeders can develop a line that increases the economic worth of its hybrids over that of hybrids made with either parent.

If the number of loci segregating in a cross between two inbred lines is n, the number of unique genotypes in the $F_2$ generation is $3^n$ and the number of unique inbred lines from this cross is $\{(2^n)-2\}$. Only a very limited number of these combinations are useful. Only about 1 in 10,000 of the progeny from $F_2$'s are commercially useful.

By way of example, if it is assumed that the number of segregating loci in $F_2$ is somewhere between 20 and 50, and that each parent is fixed for half the favorable alleles, it is then possible to calculate the approximate probabilities of finding an inbred that has the favorable allele at $\{(n/2)+m\}$ loci, where n/2 is the number of favorable alleles in each of the parents and m is the number of additional favorable alleles in the new inbred. See Example 2 below. The number m is assumed to be greater than three because each allele has so small an effect that evaluation techniques are not sensitive enough to detect differences due to three or less favorable alleles. The probabilities in Example 2 are on the order of $10^{-5}$ or smaller and they are the probabilities that at least one genotype with (n/2)=m favorable alleles will exist.

To put this in perspective, the number of plants grown on 60 million acres at 25,000 plants/acre is $1.5 \times 10^{12}$.

EXAMPLE 2

Probability of finding an inbred with m of n favorable alleles

Assume each parent has n/2 of the favorable alleles and only ½ of the combinations of loci are economically useful.

| No. of segregating loci (n) | No. of favorable alleles in Parents (n/2) | No. additional favorable alleles in new inbred | Probability that genotype occurs* |
|---|---|---|---|
| 20 | 10 | 14 | $3 \times 10^{-5}$ |
| 24 | 12 | 16 | $2 \times 10^{-5}$ |
| 28 | 14 | 18 | $1 \times 10^{-5}$ |
| 32 | 16 | 20 | $8 \times 10^{-6}$ |
| 36 | 18 | 22 | $5 \times 10^{-6}$ |
| 40 | 20 | 24 | $3 \times 10^{-6}$ |
| 44 | 22 | 26 | $2 \times 10^{-6}$ |
| 48 | 24 | 28 | $1 \times 10^{-6}$ |

*Probability that a useful combination exists, does not include the probability of identifying this combination if it does exist.

The possibility of having a usably high probability of being able to identify this genotype based on replicated field testing would be most likely smaller than this, and is a function of how large a population of genotypes is tested and how testing resources are allocated in the testing program.

Pioneer research station staff propose about 400 to 500 new inbreds each year from over 2,000,000 pollinations. Of those proposed new inbreds, less than 50, and more commonly less than 30, are actually selected for commercial use.

SUMMARY OF THE INVENTION

According to the invention, there is provided a hybrid sunflower plant, designated as 63A51, produced by crossing two Pioneer Hi-Bred International, Inc. proprietary inbred sunflower lines. This invention thus relates to the hybrid seed 63A51, the hybrid plant produced from the seed, and variants, mutants and trivial modifications of hybrid 63A51. Pioneer Brand Hybrid 63A51 is a single cross, oleic oil type sunflower hybrid. Hybrid 63A51 has demonstrated an unexpected yield for its maturity and oil type with superior root strength and stalk qualities. It is a medium-early maturing hybrid that has shown to be adapted to sunflower growing regions of Canada, the northern and central Plains of the U.S., and regions of western Europe. It has good stable yield across environments, with specific resistance to Downy Mildew (Races 1 & 2) and tolerances to Verticillium wilt and Macrophomina stalk rot. The oil quality obtained from this hybrid yields one with 90% oleic acid.

DEFINITIONS

In the description and examples that follow, a number of terms are used herein. In order to provide a clear and consistent understanding of the specification and claims, including the scope to be given such terms, the following definitions are provided. NOTE: ABS is in absolute terms and %MN is percent of the mean for the experiments in which the inbred or hybrid was grown. These designators will follow the descriptors to denote how the values are to be interpreted. Below are the descriptors used in the data tables included herein.

$/ACR=A calculated trait of the value of oil obtained. Yield (LBS/10) multiplied by the percent oil (OIL10P) multiplied by the average cost paid for sunflower.

50PFLW—The number of days it takes for 50 percent of the plants to reach the stage of R5.1 R5.1 is when the ray flowers are visible and the first ring of disk flowers has emerged and flowered.

BNKSC—A 1 to 9 visual rating indicating the level of neck breakage. The higher the score the less breakage that occurs.

BSKSC—A 1 to 9 visual rating indicating the level of stalk breakage. The higher the score the less breakage that occurs.

CLD TST=COLD TEST. The percent of plants that germinate under cold test conditions.

CTRSET=A 1 to 9 visual rating indicating the degree of seed set obtained within the sunflower head. A 1 equals a head where only the outer 10% of the head sets seed. A 9 equals a head where 90–100% of the head sets seed.

CYTOPLASMIC MALE STERILE (CMS) PLANT OR INBRED LINE. A sunflower line that produces no viable pollen is called male sterile. Male sterility is inherited maternally, i.e. the male sterile plant is used as the female parent in a cross with pollen from another sunflower. CMS lines are produced by crossing a maintainer line with a sunflower plant with the cytoplasmic male sterility trait and then backcrossing to the maintainer line until a male sterile line that is homologous to the maintainer line in all other respects is developed. CMS lines are also referred to as female lines.

D/D=DRYDOWN. This represents the relative rate at which a hybrid will reach acceptable harvest moisture compared to other hybrids on a 1–9 rating scale. A high score indicates a hybrid that dries relatively fast while a low score indicates a hybrid that dries slowly.

DNYMLW=A 1 to 9 visual rating indicating the resistance to Downy Mildew (*Plasmopara halstedii*). A higher score indicates greater resistance.

DYSR9=The number of days it takes for 50 percent of the plants to reach the R9 flowering stage. This is a stage of physiological maturity that is determined when the back of the flowering head has reached a yellowing stage and the outer bracts of the head have started to brown. This normally is a stage when the seed moisture is at about 30–40% moisture.

HARHT=This is the height of the head at harvest, measured in decimeters.

HARMST=This is a measure of seed moisture taken at harvest time. It is recorded in percentage of moisture to seed weight.

LBS/10=The grain yield as measured in pounds divided by 10.

OIL10P=The percentage of oil content measured from the harvested grain adjusted to a 10% moisture level.

PHOSC=A 1 to 9 visual rating indicating the resistance to Phompsis stalk rot (*Phompsis helianthii*). A higher score indicates a greater resistance.

PLTHT=This is the height of the head at flowering, measured in decimeters.

PMASC=A 1 to 9 visual rating indicating the resistance to Phoma stalk rot (*Phoma macdonaldii*. The higher score indicates a greater resistance.

R160=A measure of the percentage of Palmitic acid found in the oil of the seed as measured by a rapid reading from a gas chromatograph.

R180=A measure of the percentage of Stearic acid found in the oil of the seed as measured by a rapid reading from a gas chromatograph.

R181=A measure of the percentage of Oleic acid found in the oil of the seed as measured by a rapid reading from a gas chromatograph.

R182=A measure of the percentage of Linoleic acid found in the oil of the seed as measured by a rapid reading from a gas chromatograph.

RESTORER LINE. A line possessing the gene or genes to restore male fertility or viable pollen to a sunflower hybrid or inbred line and progeny having a maternal cytoplasm that conditions male sterility. This term is also discussed in the literature. See for e.g. Fick, "Breeding and Genetics," in Sunflower Science and Technology 279–338 (J. F. Carter ed. 1978), the contents of which are incorporated herein by reference.

RLGSC=A 1 to 9 visual rating indicating the level of root lodging. The higher the score the less root lodging that occurs.

RSTSC=A 1 to 9 visual rating indicating the resistance to Rust (*Puccinia helianthii*). A higher score indicates greater resistance.

SCLHSC=A 1 to 9 visual rating indicating the resistance to Sclerotinia (*Sclerotinia sclerotiorum*), head infection. A higher score indicates a greater resistance.

SCLRSC=A 1 to 9 visual rating indicating the resistance to Sclerotinia (*Sclerotinia sclerotiorum*), root and basal stalk infection. A higher score indicates a greater resistance.

SLFFER=A 1 to 9 visual rating indicating the detree of self fertility found within a self pollinated head. A score of 1 indicates <10% of the seed sets under a bagged self. A score of 9 indicates that 90–100% of the seed sets under a bagged self.

STA GRN=STAY GREEN. Stay green is the measure of plant health near the time of black layer formation (physiological maturity). A high score indicates better late-season plant health.

STMCRV=A 1 to 9 visual rating indicating the degree of stem curvature and head ttitude. A 1 indicates a very pendulous neck and head whereas a 9 indicates virtually no neck bend and an erect head attitude.

SUNFLOWER SEED. Botanically referred to as an "achene", comprised of the pericarp and embryo.

VERWLT=A 1 to 9 visual rating indicating the resistance to Verticillium wilt (*Verticillium dahliae*). A higher score indicates a greater resistance.

DETAILED DESCRIPTION OF THE INVENTION

Pioneer Brand Hybrid is a single cross, oleic oil type sunflower hybrid. Hybrid 63A51 has demonstrated an unexpected yield for its maturity and oil type with superior root strength and stalk qualities. It is a medium-early maturing hybrid that has shown to be adapted to sunflower growing regions of Canada, the northern and central Plains of the U.S., and regions of western Europe. It has good stable yield across environments, with specific resistance to Downy Mildew (Races 1 & 2) and tolerances to Verticillium wilt and Macrophomina stalk rot. It has good tolerance to common Rust. It is moderately susceptible to both head and root infections of Sclerotinia. It has average oil content. The oil quality obtained from this hybrid yields one with 90% oleic acid. The plants have moderately erect heads and medium height and have average resistance to root and stalk lodging.

This hybrid has the following characteristics based on the data collected primarily at Woodland, Calif.

TABLE 1

VARIETY DESCRIPTION INFORMATION
HYBRID-PIONEER HYBRID 63A51

| | | |
|---|---|---|
| Class: Oil Type | Region Best Adapted: Sunflower growing regions of the U.S.A., Canada, northern and western Europe | |
| A. Maturity: | | |
| Head First Visible (from emergence): | 69 | |
| Harvest Ripeness: | 110 | |
| B. Plant Characteristics: | | |
| Plant height: | 189 cm | |
| C. Stem: | | |
| Length of Internode at Harvest Ripeness: | 4.9 cm | |
| Number of Leaves: | 38 | |
| Branching: | None | |
| Color of Growing Point: | Green | |
| D. Leaves: | | |
| Blade Length: | 28.0 cm | |
| Blade Width: | 26.0 cm | |
| Width:Length Ratio: | Narrower than long | |
| Leaf Shape: | Cordate | |
| Leaf Apex: | Acuminate | |
| Leaf Base: | Auriculate | |
| Leaf Margin: | Moderately coarsely dentate | |

TABLE 1-continued

VARIETY DESCRIPTION INFORMATION
HYBRID-PIONEER HYBRID 63A51

| | | |
|---|---|---|
| Depth of Margin Indentation: | Intermediate | |
| Attitude: | Horizontal | |
| Surface: | Crinkled (ridged), lightly | |
| Color: | Green | |
| Margin Color: | Green | |
| E. Head at Flowering: | | |
| Ray Flowers: | Present | |
| Ray Flower Color: | Yellow | |
| Disk Flower Color: | Yellow | |
| Anthocyanin in Stigmans: | Absent | |
| Pollen Color: | Yellow | |
| Pappi: | Green | |
| Ray Length: | 80 mm | |
| Ray Width: | 21 mm | |
| F. Head at Seed Maturity: | | |
| Diameter: | 24 cm | |
| Receptacle Shape: | Convex | |
| Head Attitute: | Slightly Descending | |
| Seeds Per Head | 1500 | |
| G. Seeds: | | |
| Outer Pericarp: | Striped Black | |
| Middle Pericarp: | White | |
| Inner Pericarp (seed coat): | No Color | |
| Stripes: | Black with narrow Dark-Grey Striping | |
| Mottling: | Absent | |
| Shape: | Narrowly Obovate | |
| Shape (cross section) | Curved | |
| Length | 16 mm | |
| 100 seed | 9.0 grams | |
| % Held on 7.9 mm (20/64) Round-Hole Screen | 0.0 | |
| H. Diseases: | | |
| Downy Mildew (*P. halstedii*): | Resistant (Races 1 & 2) | |
| Rust: (*P. helinathii*): | Tolerant | |
| Verticillium Wilt (*V. dahliae*): | Moderate Resistant | |
| White Blister Rust (*A. tragopogi*): | Susceptible | |
| Broomrape (*O. cumanii*): | Susceptible | |
| Sclerotinia Wilt (*S. sclerotiorum*): | Susceptible | |
| Leaf Mottle (*V. albo-atrum*): | Not Tested | |
| Gray-Mold Blight, Bud Rot (*B. cinerea*): | Not Tested | |
| Charcoal Rot, Stem Rot (*M. phaseolina*): | Moderate Resistance | |
| I. Insects: | | |
| European Sunflower Moth (*H. nebullela*): | Not Tested | |
| Sunflower Moth (*H. electellum*): | Not Tested | |
| J. Variety Most Closepy Resembling: | 6415HO | |
| Frost Resistance: | Same as | |
| Lodging Resistance: | Superior to | |
| Neck or Stem Strength: | Superior to | |
| Branching Type: | Same as | |
| Petiole length: | Less than | |
| Leaf Shape: | Same as | |
| Leaf Color: | Same as | |
| Leaf Attitude: | Same as | |
| Head Attitude: | Superior to | |
| Ray Flower Color: | Same as | |
| Seed Shape: | Same as | |
| Seed Color: | Same as | |
| Seed Striping Pattern: | Same as | |
| Seed Yield: | Superior to | |
| % Oil | 43% vs. 45% | |
| % Oleic Acid | 90% vs. 88% | |
| % Linoleic Acid | 2% vs. 3% | |

*In interpreting the foregoing color designations, reference may be had to the Munsell Glossy Book of Color, a standard color reference.
Data collected from plots in Woodland, California in 1995 and Moorhead, Minnesota in 1966.
(PVP Certificate No.) is a Pioneer Hi-Bred International, Inc. proprietary hybrid.

Research Comparisons for Pioneer Hybrid 63A51

Table 2A is a paired comparison analysis of 63A51 compared with a similarly adapted Sunflower, 6400. The results show that 63A51 is slightly earlier maturing and is higher yielding than 6400. 63A51 demonstrates superior broken neck and broken stalk scores, and has a higher oleic acid content than 6400.

Table 2B is a paired comparison analysis of 63A51 compared with a similarly adapted high oleic Sunflower, 6415. The results show that 63A51 is earlier maturing and is higher yielding than 6415. 63A51 demonstrates superior root and stalk scores and has a higher oleic acid content than 6415.

Table 2C is a paired comparison analysis of 63A51 compared with a similarly adapted Sunflower, 6451. The results show that 63A51 is slightly earlier maturing than 6400. Both hybrids are high yielding.

Table 2D is a paired comparison analysis of 63A51 compared with a similarly adapted Mycogen Sunflower, 846. The results show that 63A51 is significantly higher yielding than 6400. 63A51 demonstrates superior stalk and root strength and has higher oleic acid content than 846.

TABLE 2A

PAIRED COMPARISON REPORT
VARIETY #1 - P63A51
VARIETY #2 - P6400

|  | VAR # | LBS /10 ABS | OIL 10P ABS | $/ ACR ABS | TST WTE ABS | HAR MST ABS | 50P FLW ABS | DYS R9 ABS | SLF FER ABS | PLT HT ABS | STM CRV ABS | BNK SC ABS |
|---|---|---|---|---|---|---|---|---|---|---|---|---|
| TOTAL SUM | 1 | 245.8 | 43.3 | 307.2 | 30.2 | 11.4 | 70.8 | 108.0 | 7.2 | 16.6 | 7.3 | 8.1 |
|  | 2 | 195.7 | 44.4 | 249.6 | 28.6 | 11.0 | 71.8 | 110.0 | 6.6 | 15.9 | 6.0 | 2.4 |
|  | LOCS | 12 | 7 | 7 | 11 | 12 | 4 | 1 | 4 | 4 | 3 | 4 |
|  | REPS | 31 | 16 | 16 | 29 | 31 | 8 | 3 | 8 | 8 | 5 | 8 |
|  | DIFF | 50.0 | 1.1 | 57.6 | 1.7 | 0.4 | 0.9 | 2.0 | 0.6 | 0.7 | 1.3 | 5.8 |
|  | PROB | .000# | .023+ | .015+ | .001# | .402 | .076* |  | .412 | .320 | .057* | .001# |

|  | VAR # | BSK SC ABS | RLG SC ABS | CTR SET ABS | PCT VER ABS | SCL RSC ABS | SCL HSC ABS | R16 0 ABS | R18 0 ABS | R18 1 ABS | R18 2 ABS |
|---|---|---|---|---|---|---|---|---|---|---|---|
| TOTAL SUM | 1 | 8.0 | 7.1 | 8.5 | 93.0 | 7.6 | 6.8 | 3.0 | 3.7 | 89.3 | 3.7 |
|  | 2 | 7.8 | 7.6 | 7.5 | 95.0 | 7.6 | 7.0 | 4.1 | 3.5 | 66.7 | 25.3 |
|  | LOCS | 8 | 6 | 2 | 1 | 5 | 2 | 2 | 2 | 2 | 2 |
|  | REPS | 15 | 13 | 2 | 2 | 10 | 6 | 2 | 2 | 2 | 2 |
|  | DIFF | 0.2 | 0.5 | 1.0 | 2.0 | 0.0 | 0.2 | 1.1 | 0.2 | 22.6 | 21.6 |
|  | PROB | .618 | .154 | .500 |  | 1.00 | .795 | .261 | .216 | .265 | .272 |

*= 10% SIG
+= 5% SIG
= 1% SIG

TABLE 2B

PAIRED COMPARISON REPORT
VARIETY #1 - P63A51
VARIETY #2 - P6415HO

|  | VAR # | LBS /10 ABS | OIL 10P ABS | $/ ACR ABS | TST WTE ABS | HAR MST ABS | 50P FLW ABS | DYS R9 ABS | SLF FER ABS | PLT HT ABS | STM CRV ABS | BNK SC ABS |
|---|---|---|---|---|---|---|---|---|---|---|---|---|
| TOTAL SUM | 1 | 219.2 | 43.2 | 283.7 | 30.7 | 11.5 | 68.8 | 113.5 | 7.3 | 17.0 | 7.4 | 7.6 |
|  | 2 | 212.8 | 45.4 | 273.3 | 31.2 | 12.3 | 71.8 | 113.1 | 7.2 | 17.5 | 6.0 | 7.2 |
|  | LOCS | 23 | 11 | 10 | 15 | 23 | 8 | 5 | 5 | 8 | 5 | 5 |
|  | REPS | 155 | 26 | 23 | 36 | 55 | 12 | 8 | 9 | 13 | 7 | 10 |
|  | DIFF | 6.4 | 22 | 10.4 | 0.5 | 0.7 | 3.0 | 0.4 | 0.1 | 0.5 | 1.4 | 0.4 |
|  | PROB | .402 | .000# | .398 | .181 | .067* | .000# | .648 | .822 | .502 | .005# | .456 |

|  | VAR # | BSK SC ABS | RLG SC ABS | CTR SET ABS | PCT VER ABS | SCL RSC ABS | SCL HSC ABS | R16 0 ABS | R18 0 ABS | R18 1 ABS | R18 2 ABS |
|---|---|---|---|---|---|---|---|---|---|---|---|
| TOTAL SUM | 1 | 8.1 | 7.3 | 8.5 | 93.0 | 7.6 | 5.2 | 3.0 | 3.7 | 89.3 | 3.7 |
|  | 2 | 8.3 | 7.2 | 7.0 | 95.0 | 6.8 | 5.5 | 3.0 | 4.6 | 87.4 | 4.8 |
|  | LOCS | 9 | 11 | 2 | 1 | 5 | 4 | 2 | 2 | 2 | 2 |
|  | REPS | 17 | 24 | 2 | 2 | 10 | 11 | 2 | 2 | 2 | 2 |
|  | DIFF | 0.2 | 0.1 | 1.5 | 2.0 | 0.8 | 0.4 | 0.1 | 0.8 | 1.9 | 1.1 |
|  | PROB | .532 | .702 | .205 |  | .317 | .712 | .656 | .068* | .403 | .553 |

*= 10% SIG
+= 5% SIG
= 1% SIG

TABLE 2C

PAIRED COMPARISON REPORT
VARIETY #1 - P63A51
VARIETY #2 - P6451

|  | VAR # | LBS /10 ABS | OIL 10P ABS | $/ ACR ABS | TST WTE ABS | HAR MST ABS | 50P FLW ABS | DYS R9 ABS | SLF FER ABS | PLT HT ABS | STM CRV ABS | BNK SC ABS | BSK SC ABS | RLG SC ABS | SCL HSC ABS |
|---|---|---|---|---|---|---|---|---|---|---|---|---|---|---|---|
| TOTAL SUM | 1 | 210.3 | 42.8 | 268.2 | 30.9 | 11.5 | 67.9 | 114.8 | 7.9 | 17.5 | 7.3 | 5.5 | 8.7 | 7.5 | 5.2 |
|  | 2 | 212.4 | 46.2 | 251.8 | 29.7 | 11.4 | 70.1 | 115.3 | 7.3 | 17.3 | 7.0 | 4.5 | 8.5 | 7.9 | 2.6 |
|  | LOCS | 19 | 7 | 6 | 12 | 19 | 6 | 4 | 3 | 6 | 3 | 1 | 2 | 7 | 4 |
|  | REPS | 46 | 17 | 14 | 30 | 47 | 10 | 6 | 7 | 11 | 5 | 2 | 5 | 17 | 11 |
|  | DIFF | 2.1 | 3.4 | 16.4 | 1.2 | 0.1 | 2.2 | 0.5 | 0.6 | 0.2 | 0.3 | 1.0 | 0.2 | 0.4 | 2.6 |
|  | PROB | .851 | .006# | .426 | .007# | .728 | .000# | .836 | .560 | .816 | .423 |  | .500 | .097* | .082* |

*= 10% SIG
+= 5% SIG
= 1% SIG

TABLE 2D

PAIRED COMPARISON REPORT
VARIETY #1 - P63A51
VARIETY #2 - -MYTSN846

|  | VAR # | LBS /10 ABS | OIL 10P ABS | $/ ACR ABS | TST WTE ABS | HAR MST ABS | 50P FLW ABS | DYS R9 ABS | SLF FER ABS | PLT HT ABS | STM CRV ABS | BNK SC ABS |
|---|---|---|---|---|---|---|---|---|---|---|---|---|
| TOTAL SUM | 1 | 224.6 | 43.9 | 293.1 | 30.3 | 11.6 | 69.6 | 114.8 | 7.2 | 16.8 | 7.3 | 8.1 |
|  | 2 | 195.7 | 43.2 | 243.6 | 29.2 | 10.7 | 70.9 | 114.8 | 6.5 | 15.8 | 5.8 | 4.5 |
|  | LOCS | 17 | 8 | 8 | 12 | 17 | 6 | 2 | 4 | 6 | 4 | 4 |
|  | REPS | 38 | 18 | 18 | 30 | 38 | 10 | 3 | 8 | 11 | 6 | 8 |
|  | DIFF | 28.9 | 0.7 | 49.5 | 1.1 | 0.8 | 1.3 | 0.0 | 0.7 | 1.0 | 1.5 | 3.6 |
|  | PROB | .010+ | .018+ | .025+ | .025+ | .001# | .062* | 1.00 | .382 | .257 | .014+ | .013+ |

|  | VAR # | BSK SC ABS | RLG SC ABS | CTR SET ABS | PCR VER ABS | SCL RSC ABS | SCL HSC ABS | R16 0 ABS | R18 0 ABS | R18 1 ABS | R18 2 ABS |
|---|---|---|---|---|---|---|---|---|---|---|---|
| TOTAL SUM | 1 | 8.0 | 7.1 | 8.5 | 93.0 | 7.6 | 4.9 | 3.0 | 3.7 | 89.3 | 3.7 |
|  | 2 | 7.6 | 6.8 | 7.0 | 97.0 | 7.5 | 5.6 | 3.1 | 4.1 | 87.2 | 5.3 |
|  | LOCS | 8 | 8 | 2 | 1 | 5 | 3 | 2 | 2 | 2 | 2 |
|  | REPS | 15 | 16 | 2 | 2 | 10 | 8 | 2 | 2 | 2 | 2 |
|  | DIFF | 0.4 | 0.4 | 1.5 | 4.0 | 0.1 | 0.7 | 0.2 | 0.3 | 2.1 | 1.7 |
|  | PROB | .491 | .390 | .205 |  | .704 | .478 | .467 | .808 | .587 | .446 |

*= 10% SIG
+= 5% SIG
= 1% SIG

Comparison of Key Characteristics for Hybrid 63A51

Table 3 compares key characteristics between Sunflower hybrids 63A51 and other similarly adapted high oleic sunflowers, OLOMIL and OLMARIL. According to the results, 63A51 is higher yielding than all of the hybrids compared. 63A51 is also superior for stalk breakage than all of the compared hybrids. 63A51's high yield combined with its other favorable agronomic traits make it a valuable hybrid to its area of adaptation.

TABLE 3

HYBRID CHARACTERISTICS CHART

| TRAITS | OLOMIL | OLMARIL | 63A51 |
|---|---|---|---|
| YIELD | 7 | 8 | 9 |
| YLD/MAT | 5 | 6 | 7 |
| MAT | MED | MED | MED |
| FLW | 67 | 68 | 66 |
| RM | 41 | 42 | 40 |

TABLE 3-continued

HYBRID CHARACTERISTICS CHART

| TRAITS | OLOMIL | OLMARIL | 63A51 |
|---|---|---|---|
| PM40%(S) | 93 | 95 | 91 |
| PM40%(R) |  |  | 115 |
| DAYSHAR |  |  | 121 |
| OIL10P | 8 | 8 | 7 |
| DRYDWN | 7 | 7 | 6 |
| SLFFER | 7 | 9 | 8 |
| PLTHT | 4 | 4 | 4 |
| STMCRV | 6 | 6 | 8 |
| SDVGR | 7 | 8 | 7 |
| BNKSC | S | 6 | 6 |
| BSKSC | 6 | 7 | 9 |
| RLGSC | 6 | 6 | 8 |
| CTRSET | 7 | 8 | 8 |
| SEDPAC | 8 | 8 | 8 |
| RUSTSC | 4 | 5 | 5 |
| PMASC | 4 | 6 | 5 |
| RTSCL | 4 | 5 | 4 |
| HDSCL | 4 | 5 | 4 |

TABLE 3-continued

HYBRID CHARACTERISTICS CHART

| TRAITS | OLOMIL | OLMARIL | 63A51 |
|---|---|---|---|
| BDSCL | 5 | | |
| STKSCL | 4 | | |
| VERTSC | 4 | 5 | 5 |
| BRMSC | 1 | 1 | 1 |
| DM2SC | 9 | 9 | 9 |
| PHOSC | 4 | 4 | |
| 8OTSC | 5 | | |
| DRTTOL | | | |
| R181SC | 8 | 8 | 8 |
| PCT020 | | | |
| PCT014 | | | |
| SEDLSC | | | |
| SDCSC | | | |
| PCTKER | | | |

INDUSTRIAL APPLICABILITY

This invention includes hybrid sunflower seed of 63A51 and the hybrid sunflower plant produced therefrom. The foregoing was set forth by way of example and is not intended to limit the scope of the invention.

As used herein, the term plant includes plant cells, plant protoplasts, plant cell tissue cultures from which sunflower plants can be regenerated, plant calli, plant clumps, and plant cells that are intact in plants, or parts of plants, such as embryos, pollen, ovules, flowers, leaves, seeds, husks, stalks, roots, root tips, anthers, and the like.

Duncan, Williams, Zehr, and Widholm, Planta, (1985) 165:322–332 reflects that 97% of the plants cultured which produced callus were capable of plant regeneration. Subsequent experiments with both inbreds and hybrids produced 91% regenerable callus which produced plants. In a further study in 1988, Songstad, Duncan & Widholm in Plant Cell Reports (1988), 7:262–265 reports several media additions which enhance regenerability of callus of two inbred lines. Other published reports also indicated that "nontraditional" tissues are capable of producing somatic embryogenesis and plant regeneration. Thus, it is clear from the literature that the state of the art is such that these methods of obtaining plants are, and were, "conventional" in the sense that they are routinely used and have a very high rate of success. Thus, another aspect of this invention is to provide cells which upon growth and differentiation produce sunflower plants having the genotype of 63A51.

Sunflower (*Heliathus annuus*) oil is a major edible oil worldwide. The oil component of sunflower seeds typically contributes about 80 percent of the value of a sunflower crop and is mostly used as a cooking medium. Sunflower oil is also used as salad oil, as well as in the manufacture of margarine, soap, shortening, lubricants, and as a source for biodiesel fuels. In the United States, approximately 4 million acres are planted in sunflowers annually, primarily in the Dakotas and Minnesota. In addition, the seed of hybrid sunflower line 63A51 can be utilized for human food and animal feed.

Although the foregoing invention has been described in some detail by way of illustration and example for purposes of clarity and understanding, it will be obvious that certain changes and modifications may be practiced within the scope of the invention, as limited only by the scope of the appended claims.

DEPOSITS

Applicant has made a deposit of at least 2500 seeds of Hybrid Sunflower Line 63A51 with the American Type Culture Collection (ATCC), Manassas, Va. 20110 USA, ATCC Deposit No. 203054. The seeds deposited with the ATCC on Jul. 10, 1998 were taken from the deposit maintained by Pioneer Hi-Bred International, Inc., 700 Capital Square, 400 Locust Street, Des Moines, Iowa. 50309–2340 since prior to the filing date of this application. This deposit of the Hybrid Sunflower Line 63A51 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has satisfied all the requirements of 37 C.F.R. §§1.801–1.809, including providing an indication of the viability of the sample. Applicant imposes no restrictions on the availability of the deposited material from the ATCC; however, Applicant has no authority to waive any restrictions imposed by law on the transfer of biological material or its transportation in commerce. Applicant does not waive any infringement of its rights granted under this patent.

What is claimed is:

1. Hybrid sunflower seed designated 63A51, representative seed of said hybrid 63A51 having been deposited under ATCC accession number 203054.

2. A sunflower plant, or its parts, produced by the seed of claim 1.

3. Pollen of the plant of claim 2.

4. An ovule of the plant of claim 2.

5. A tissue culture of regenerable cells of a hybrid sunflower plant 63A51, wherein the tissue regenerates plants, said plants capable of expressing all the morphological and physiological characteristics of 63A51, representative seed having been deposited under ATCC accession number 203054.

6. A tissue culture according to claim 5, the cells or protoplasts being from a tissue selected from the group consisting of leaves, pollen, embryos, roots, root tips, anthers, silks, flowers, and stalks.

7. A sunflower plant, or its parts, regenerated from the tissue culture of claim 5 and capable of expressing all the morphological and physiological characteristics of 63A51, representative seed having been deposited under ATCC accession number 203054.

* * * * *

UNITED STATES PATENT AND TRADEMARK OFFICE
CERTIFICATE OF CORRECTION

PATENT NO : 5,866,765

DATED : Feb. 2, 1999

INVENTOR(S): Glenn S. Cole

It is certified that error appears in the above-identified patent and that said Letters Patent are hereby corrected as shown below:

On the face sheet of the patent, for Appl. No., delete "783,915" and insert --08/783,915--.

In column 14, line 12, delete "Va." and insert --VA--.

In column 14, line 14, delete "Jul." and insert --July--.

Signed and Sealed this

First Day of May, 2001

Attest:

NICHOLAS P. GODICI

Attesting Officer

Acting Director of the United States Patent and Trademark Office